(12) United States Patent  
Nitto (10) Patent No.: US 11,703,493 B2  
(45) Date of Patent: Jul. 18, 2023

(54) INFORMATION PROCESSING APPARATUS, INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventor: Yuuichi Nitto, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 124 days.

(21) Appl. No.: 17/194,679

(22) Filed: Mar. 8, 2021

(65) Prior Publication Data

US 2021/0285924 A1 Sep. 16, 2021

(30) Foreign Application Priority Data

Mar. 13, 2020 (JP) .................................. 2020-044387

(51) Int. Cl.
| | |
|---|---|
| *G01N 33/00* | (2006.01) |
| *G06F 3/14* | (2006.01) |
| *A01D 46/28* | (2006.01) |
| *G08B 5/22* | (2006.01) |
| *G06F 3/0482* | (2013.01) |

(52) U.S. Cl.
CPC ......... *G01N 33/0098* (2013.01); *A01D 46/28* (2013.01); *G06F 3/14* (2013.01); *G08B 5/22* (2013.01); *G06F 3/0482* (2013.01)

(58) Field of Classification Search
USPC ....................................................... 340/691.6
See application file for complete search history.

(56) References Cited

U.S. PATENT DOCUMENTS

| | | | |
|---|---|---|---|
| 10,129,457 B2 | 11/2018 | Nitto | |
| 2014/0288850 A1* | 9/2014 | Avigdor | G05B 15/02 702/19 |
| 2016/0330906 A1* | 11/2016 | Acheson | A01D 41/127 |
| 2018/0020622 A1* | 1/2018 | Richt | G06Q 50/02 703/6 |
| 2019/0150357 A1* | 5/2019 | Wu | H04N 7/188 |
| 2019/0179982 A1* | 6/2019 | Reese | G06F 30/20 |
| 2020/0196535 A1* | 6/2020 | Dagondon | A01G 9/18 |
| 2021/0287001 A1* | 9/2021 | Meltzer | G06V 20/188 |

FOREIGN PATENT DOCUMENTS

JP 2019-041613 A 3/2019

\* cited by examiner

*Primary Examiner* — Omar Casillashernandez (74) *Attorney, Agent, or Firm* — Carter, DeLuca & Farrell LLP (57) ABSTRACT

An information processing apparatus comprises a first obtaining unit configured to obtain a predicted value of a yield of crops in a section where the crops are cultivated, a second obtaining unit configured to obtain a yield of the crops harvested in the section, and a control unit configured to notify progress of harvesting of the crops in the section, which is determined based on the predicted value obtained by the first obtaining unit and the yield obtained by the second obtaining unit.

10 Claims, 8 Drawing Sheets

| DATA DATE/TIME | SECTION | DATA COORDINATE | DATA TYPE | DETAILS OF DATA |
|---|---|---|---|---|
| 2019/4/1 12:00:00 | a | (150, 150) | Bunch count | 15 |
| 2019/4/1 13:01:02 | a | (152, 150) | Bunch count | 21 |
| 2019/4/1 13:20:25 | b | (154, 150) | Bunch count | 18 |
| 2019/4/2 10:21:10 | b | (150, 160) | Bunch count | 12 |
| 2019/4/3 11:34:20 | c | (152, 160) | Bunch count | 19 |

FIG. 5B

| IDENTIFIER | PLANTED REGION | PLANTED AREA | FRUIT WEIGHT |
|---|---|---|---|
| a | (0, 0), (100, 0),... | 40000 m$^2$ | 75g |
| b | (100, 0), (150, 0),... | 30000 m$^2$ | 100g |
| c | (100, 100), (150, 100),... | 20000 m$^2$ | 120g |

FIG. 5C

| DATE/TIME | SECTION | COORDINATE | PREDICTIVE YIELD |
|---|---|---|---|
| 2019/4/1 12:00:00 | a | (10, 10) | 1500g |
| 2019/4/1 13:01:02 | a | (15, 10) | 2100g |
| 2019/4/1 13:20:25 | b | (154, 12) | 1800g |
| 2019/4/2 10:21:10 | c | (112, 106) | 1200g |
| 2019/4/3 11:34:20 | c | (145, 132) | 1900g |

INFORMATION PROCESSING APPARATUS, INFORMATION PROCESSING METHOD, AND NON-TRANSITORY COMPUTER-READABLE STORAGE MEDIUM

BACKGROUND OF THE INVENTION

Field of the Invention

The present invention relates to a technique for notifying the progress of harvesting of crops.

Description of the Related Art

In the cultivation of crops, the harvesting work is divisionally performed a number of times in accordance with the kinds of crops, the growth states, the weather, and the like. In some cases, crops are divisionally harvested even in one cultivation section, and this makes it cumbersome to manage the progress of the harvesting work. For example, the invention described in Japanese Patent Laid-Open No. 2019-41613 specifies a harvesting work region based on position information, time information, and the like in the harvesting season.

On the other hand, in the field of producing processed foods by using crops as materials such as in the cultivation of wine grapes, grasping the amount of harvested crops with respect to the total yield is in many cases more important than managing the progress of the harvesting work. In Japanese Patent Laid-Open No. 2019-41613, a geographical work progress can be presented, but it is difficult to present the progress with respect to a prospective total yield.

SUMMARY OF THE INVENTION

The present invention provides a technique for presenting the progress of harvesting of crops.

According to the first aspect of the present invention, there is provided an information processing apparatus comprising: a first obtaining unit configured to obtain a predicted value of a yield of crops in a section where the crops are cultivated; a second obtaining unit configured to obtain a yield of the crops harvested in the section; and a control unit configured to notify progress of harvesting of the crops in the section, which is determined based on the predicted value obtained by the first obtaining unit and the yield obtained by the second obtaining unit.

According to the second aspect of the present invention, there is provided an information processing method to be performed by an information processing apparatus, comprising: obtaining a predicted value of a yield of crops in a section where the crops are cultivated; obtaining a yield of the crops harvested in the section; and notifying progress of harvesting of the crops in the section, which is determined based on the predicted value of the yield of the crops in the section, and the yield of the crops harvested in the section.

According to the third aspect of the present invention, there is provided a non-transitory computer-readable storage medium storing a computer program for causing a computer to function as: a first obtaining unit configured to obtain a predicted value of a yield of crops in a section where the crops are cultivated; a second obtaining unit configured to obtain a yield of the crops harvested in the section; and a control unit configured to notify progress of harvesting of the crops in the section, which is determined based on the predicted value obtained by the first obtaining unit and the yield obtained by the second obtaining unit.

Further features of the present invention will become apparent from the following description of exemplary embodiments (with reference to the attached drawings).

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate.

Furthermore, in the attached drawings, the same reference numerals are given to the same or similar configurations, and redundant description thereof is omitted.

First Embodiment

In this embodiment, an information processing apparatus that estimates the total yield of crops expected to be harvested based on the yield (achievement data) of harvested crops, and notifies the user of the progress with respect to the total yield.

An explanation will be made by taking a case in which crops are grapes as an example. However, the following explanation is not limited to this case in which crops are grapes, and is similarly applicable to other kinds of crops.

Figure 1:
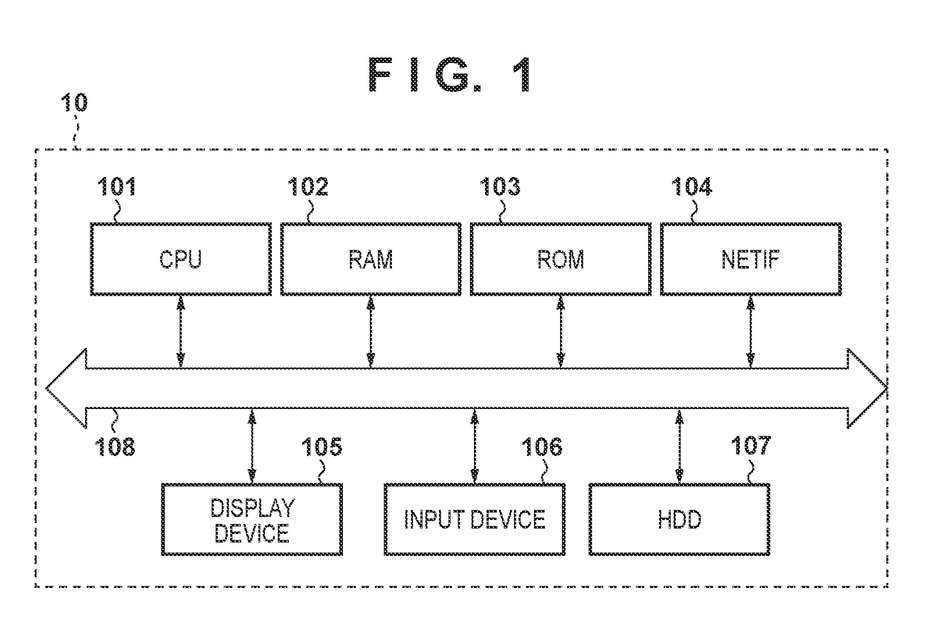
FIG. 1 is a block diagram showing a hardware configuration example of an information processing apparatus 10.

First, a hardware configuration example of an information processing apparatus 10 according to this embodiment will be explained with reference to a block diagram shown in FIG. 1. A computer apparatus such as a PC (Personal Computer), a smartphone, or a tablet terminal apparatus is applicable to the information processing apparatus 10 according to this embodiment.

A CPU (Central Processing Unit) 101 executes various processes by using computer programs and data stored in a RAM (Random Access Memory) 102 and a ROM (Read-Only Memory) 103. The CPU 101 thus controls the operation of the whole information processing apparatus 10, and executes or controls each processing to be described later as processing to be performed by the information processing apparatus 10.

The RAM 102 has an area for storing computer programs and data loaded from the ROM 103 and an HDD (Hard Disk Drive) 107, and data externally received via an NETIF (Network Interface) 104. The RAM 102 also has a work area to be used by the CPU 101 to execute various processes. As described above, the RAM 102 can appropriately provide various areas.

The ROM 103 stores setting data, a boot program, and the like of the information processing apparatus 10.

The NETIF 104 is a network interface that the information processing apparatus 10 uses to perform wired and/or wireless data communication with an external apparatus. Note that the communication with an external apparatus includes indirect communication using a relay device in addition to direct communication.

A display device 105 has a liquid crystal screen or a touch panel screen, and can display the results of processing performed by the CPU 101 by using images and characters. Note that the display device 105 may also be a projecting device such as a projector that projects images and characters.

An input device 106 is a user interface such as a keyboard, a mouse, or a touch panel screen, and the user can input various instructions to the CPU 101 by operating the input device 106. Note that the input device 106 may also have an image capturing function, and in this case the input device 106 can obtain an image captured by itself. Also, the input device 106 can have a function of obtaining an image captured by an external image capturing device.

Furthermore, the input device 106 can have one or more of various sensors such as a temperature sensor, a humidity sensor, a speed sensor, and an acceleration sensor as needed.

The HDD 107 stores an OS (Operating System), and computer programs and data for causing the CPU 101 to execute or control each processing to be described later as processing to be performed by the information processing apparatus 10. The computer programs and data stored in the HDD 107 are appropriately loaded into the RAM 102 under the control of the CPU 101, and processed by the CPU 101.

Note that the HDD 107 is an example of an external storage device for providing computer programs and data to the information processing apparatus 10, and storing various kinds of information. A device applicable to this external storage device is not limited to the HDD 107, may also be, for example, a drive device that reads out computer programs and data recorded on a recording medium. Examples of the recording medium are a flexible disk (FD), a CD-ROM, a DVD, a USB memory, an MO, and a flash memory. As the external storage device, it is also possible to apply an external server apparatus to be communicably connected to the information processing apparatus 10 across a network.

The CPU 101, the RAM 102, the ROM 103, the NETIF 104, the display device 105, the input device 106, and the HDD 107 are connected to a bus 108. Note that the display device 105 and the input device 106 need not be connected to the bus 108, and may also be communicably connected to the information processing apparatus 10 via the NETIF 104.

Figure 2:
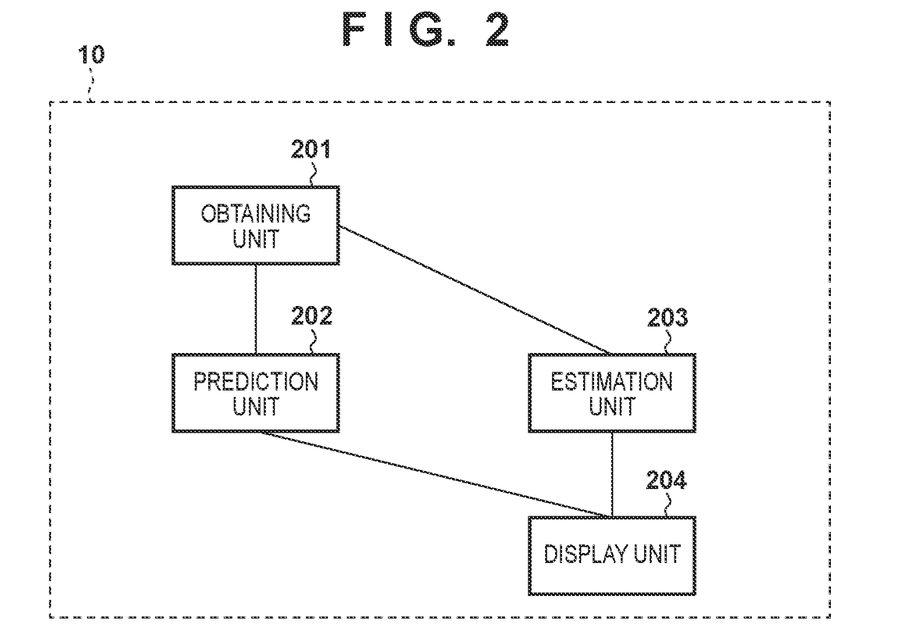
FIG. 2 is a block diagram showing a functional configuration example of the information processing apparatus 10.

FIG. 2 shows a functional configuration example of the information processing apparatus 10 according to this embodiment. The embodiment will be explained below by assuming that the functional units shown in FIG. 2 are the subjects of processing. In practice, however, the function of each functional unit is implemented by the CPU 101 by executing a computer program for causing the CPU 101 to execute the function of the functional unit. Note that each functional unit shown in FIG. 2 may also be implemented by hardware.

Figure 3:
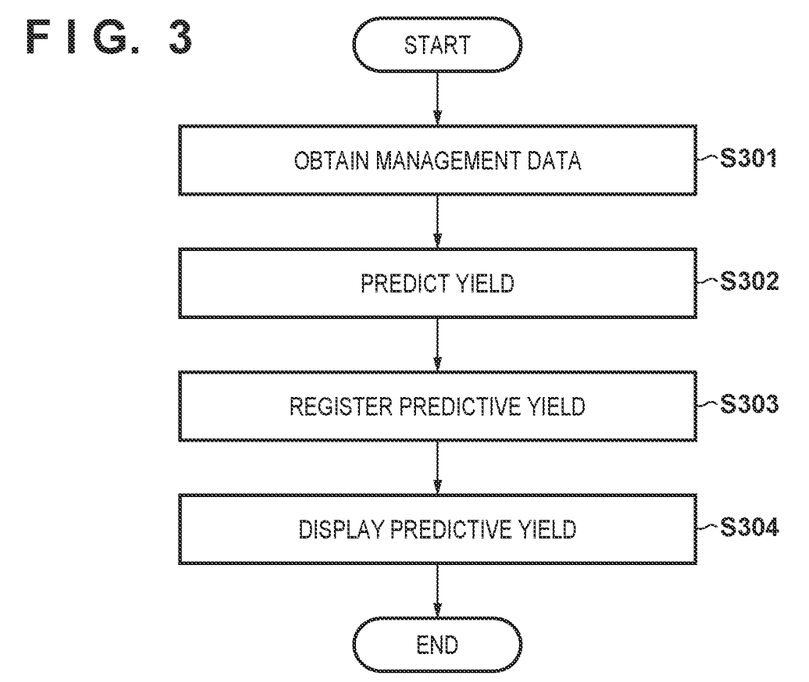
FIG. 3 is a flowchart of processing to be performed by the information processing apparatus 10.

Processing to be performed by the information processing apparatus 10 in order to present the user with the predictive yield (a predicted value of the yield) of grapes in a section selected by the user from a plurality of sections in which the grapes are cultivated will be explained below with reference to a flowchart shown in FIG. 3.

In step S301, an obtaining unit 201 obtains data for managing the growth of grapes as management data. The management data is data such as the record obtained by counting blossoms and fruits to be used to predict the yield before the grape harvesting season, or achievement information of harvesting in the past harvesting season. The management data can further contain data such as the growth state, the progress of disease and insect pest, weather information, sensor information, and the work record for growth management. The management data as described above contains data (text data and numerical data) input by the user by operating the input device 106, and data measured by various sensors such as a GPS sensor. Note that among the abovementioned data, data other than the past achievement can be managed by, for example, regularly or irregularly accepting an input of information observed in the cultivated land every day.

Figure 4:
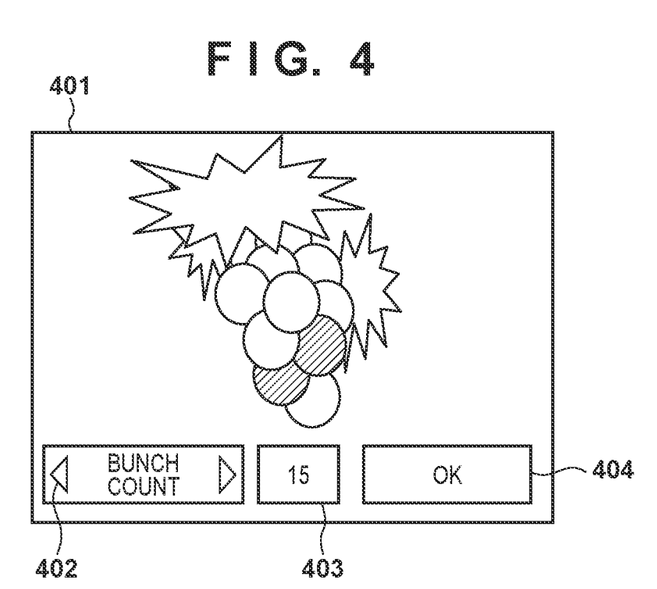
FIG. 4 is a view showing a display example of a GUI.

In this embodiment, the obtaining unit 201 displays a GUI (Graphical User Interface) 401 shown in FIG. 4 on the display device 105, and accepts an operation input from the user. The GUI 401 is used to input the number of bunches of grapes shown in a grape image captured by an image capturing device capable of measuring its own position by a sensor such as a GPS sensor. The user selects an item "bunch count" by operating an operation unit 402 by using the input device 106, and inputs "the number of bunches per unit area in a cultivation region in which grapes are cultivated" in a region 403 after that. Then, when the user selects an OK button 404 by using the input device 106, the obtaining unit 201 obtains the numerical value (bunch count) input to the region 403, and the image capturing position of a captured image displayed on the GUI 401 (that is, the position of the image capturing device measured by itself when capturing the image). Then, the obtaining unit 201 generates management data containing the obtained numerical value (bunch count) and the image capturing position, and registers the management data in a management data table. Note that in this embodiment, a grape is an example of a crop, so "bunch count" is the index of "crop count" to be used to calculate the amount of crops. However, the numerical value for handling "crop count" is not limited to "bunch count".

Figure 5A:
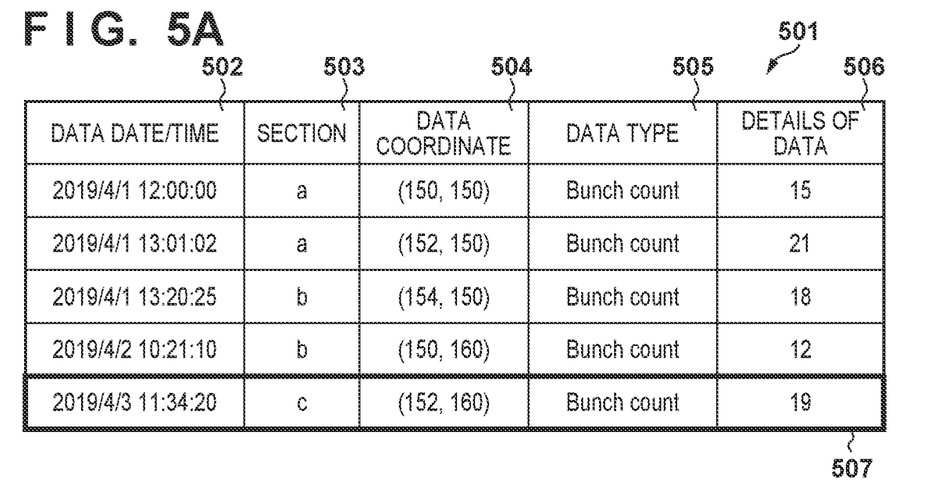
FIG. 5A is a view showing a configuration example of a management data table.

FIG. 5A shows a configuration example of the management data table according to this embodiment. A management data table 501 shown in FIG. 5A is a table registering management data in each row, and registers management data obtained for images captured in various image capturing dates and times.

In a column 502, the image capturing date/time of a captured image (that is, the date and time measured by the image capturing device when capturing the image, and obtainable from metadata added to the captured image by the image capturing device as is well known) is registered as "data date/time".

Figure 5B:
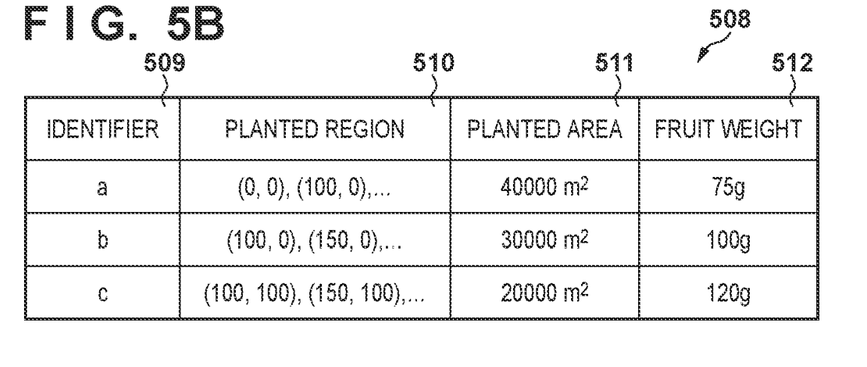
FIG. 5B is a view showing a configuration example of a section table 508.

In a column 503, the ID (section ID) unique to a section where an image is captured is registered. The cultivation region includes a plurality of sections, and grapes of the same kind are planted in the same section. FIG. 5B shows a configuration example of a section table 508 registering information defining each section. The section ID is registered in a column 509, the positions of vertices of a polygonal region when a section corresponding to the section ID is represented by the polygonal region are registered in a column 510, the area of the section corresponding to the section ID is registered in a column 511, and the weight of fruits of grapes cultivated in the section corresponding to the section ID is registered in a column 512. The section ID may also be an ID input by the user by using the input device 106. It is also possible to specify a section including the image capturing position by the information processing apparatus 10, and use the ID of the specified section as the section ID.

In a column 504, the image capturing position of the captured image (as described above, the position of the image capturing device itself when capturing the image) is registered as "data coordinates". A section including the image capturing position can be specified from the image capturing position registered in the column 504 and the positions of vertices registered in the column 510, and the section ID of the specified section is registered in the column 503. In the example shown in FIG. 5A, among a polygonal region g corresponding to section ID="a" and defined by the information (the positions of vertices) in the column 510, a polygonal region b corresponding to section ID="b" and defined by the information (the positions of vertices) in the column 510, and a polygonal region c corresponding to section ID="c" and defined by the information (the positions of vertices) in the column 510, a polygonal region including the image capturing position (152, 160) is the polygonal region c, so the section ID "c" of the polygonal region c is registered as the section ID corresponding to the image capturing position.

The type of data input by the user by using the input device 106 in relation to grapes shown in the captured image is registered in a column 505. "Bunch count" represents "the number of bunches per unit area in the cultivation region" described above.

Data input by the user by using the input device 106 in relation to grapes shown in the captured image is registered as "details of data" in a column 506. Since the data type is "Bunch count" in FIG. 5A, "the number of bunches per unit area in the cultivation region" is registered in the column 506. Note that a value to be registered in the column 506 complies with the unit or dimension corresponding to "data type" registered in the column 505.

In the example shown in FIG. 5A, management data containing image capturing date/time "2019/4/3 11:34:20", the section ID "c" of the section including the image capturing position of the image captured at this image capturing date/time, the image capturing position "(152, 160)", the data type "Bunch count" input by the user by using the input device 106 in relation to the captured image, and the data "19" is registered in a row 507 of the management data table.

Referring to FIG. 3 again, in step S302, a prediction unit 202 obtains a predicted value of the yield (a predictive yield) corresponding to management data obtained in step S301, by using the management data and the section table 508. For example, the prediction unit 202 obtains the product of "bunch count" contained in management data and "fruit weight" corresponding to the section ID contained in the management data in the section table 508, as the predictive yield corresponding to the management data. Note that this method of obtaining the predictive yield explained herein is an example, and does not intend to limited the present invention to this method.

Figure 5C:
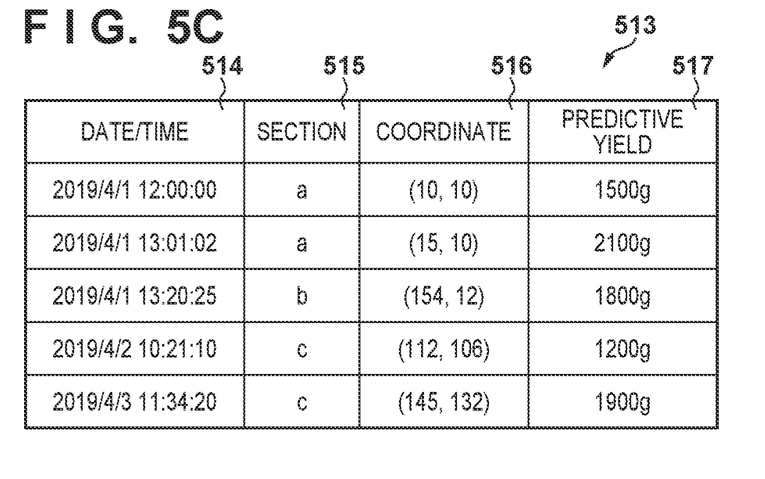
FIG. 5C is a view showing a configuration example of a predictive yield table 513.

Then, in step S303, the prediction unit 202 registers a data set containing the predictive yield obtained in step S302 in "a predictive yield table held in the HDD 107 or in an external device connected via the NETIF 104". FIG. 5C shows a configuration example of a predictive yield table 513 according to this embodiment.

An image capturing date/time contained in management data is registered in a column 514, a section ID contained in the management data is registered in a column 515, an image capturing position contained in the management data is registered in a column 516, and a predictive yield corresponding to the management data is registered in a column 517. That is, the predictive yield table 513 is a table for managing a predictive yield corresponding to each management data.

Note that when registering a data set of interest in the predictive yield table, the prediction unit 202 determines whether a data set (registered data set) containing an image capturing position whose difference from an image capturing position in the data set of interest is smaller than a threshold is registered in the predictive yield table.

If the determination result is "not registered", the prediction unit 202 registers the data set of interest in the predictive yield table. On the other hand, if the determination result is "registered", and if the difference between the image capturing date/time contained in the data set of interest and that contained in the registered data set is equal to or larger than a threshold, the prediction unit 202 registers the data set of interest in the predictive yield table. If the difference is smaller than the threshold, the prediction unit 202 does not register the data set of interest in the predictive yield table.

Figure 6:
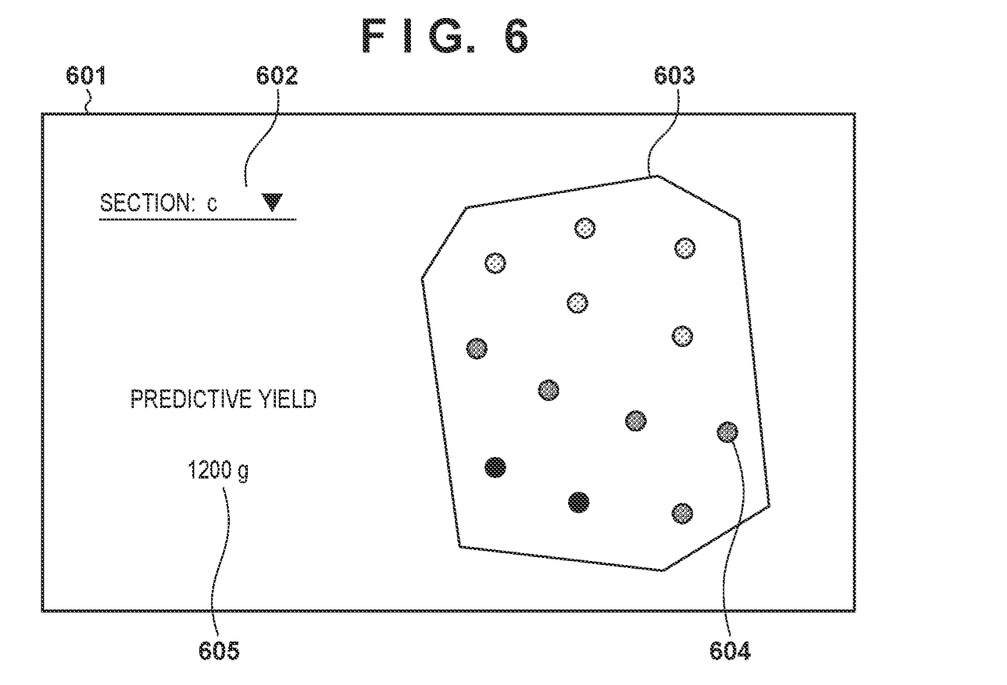
FIG. 6 is a view showing a configuration example of a screen for notifying a predictive yield.

In step S304, a display unit 204 notifies a predictive yield corresponding to a section designated by the user by using the input device 106. As one example of this embodiment, the display unit 204 generates a screen for notifying the predictive yield based on the section table 508 and the predictive yield table 513, and displays the generated screen on the display device 105. FIG. 6 shows a display example of the screen.

In a screen 601 shown in FIG. 6, the user can select a section the predictive yield of which he or she wants to see, by operating a pulldown menu 602 by using the input device 106. Referring to FIG. 6, a section (called a section c) corresponding to section ID=c is selected.

A polygon 603 is a polygonal image defined by "the positions of vertices corresponding to section ID=c" registered in the section table 508. Icons 604 are arranged in those positions on the screen, which correspond to "the image capturing positions corresponding to section ID=c" registered in the predictive yield table 513 in the polygon 603. It is also possible to change the display form such as the color or size of each icon 604 in accordance with the value of the corresponding predictive yield.

When the user designates a given icon 604 by using the input device 106, a predictive yield corresponding to the icon 604 is displayed in a region 605. In FIG. 6, an icon 604 corresponding to section ID=c and image capturing position=(112, 106) is designated, a corresponding predictive yield "1200 g" in the predictive yield table 513 shown in FIG. 5C is read out and displayed in the region 605. Note that in this example shown in FIG. 6, only the predictive yield corresponding to one point (the icon 604) particularly designated on the section c by the user is notified. However, for each icon displayed on the screen 601, it is also possible to read out one or more of the corresponding image capturing date/time, image capturing position, and predictive yield from the predictive yield table 513, and display them in the form of a list on the screen 601.

Figure 7:
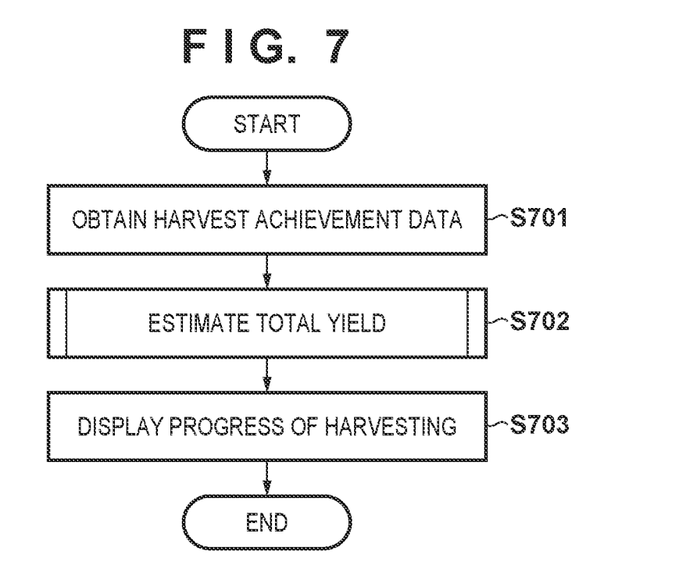
FIG. 7 is a flowchart of a process of notifying a user of the progress of harvesting.

In this embodiment, it is assumed that grapes in a cultivation region are partially harvested even in one section. A method of performing a harvesting work by dividing one section is used for various reasons matching the situation of a cultivated land. Examples are a case in which the work is performed over several days because one section is broad, and a case in which the harvesting of unmatured grapes is delayed because the growth state varies even in one section. In this embodiment, when harvesting is performed in a part of a section and the yield (harvest achievement) is input to the information processing apparatus 10, the information processing apparatus 10 notifies the user of the progress of harvesting based on the harvest achievement. This notification process will be explained in accordance with a flowchart shown in FIG. 7.

In step S701, the obtaining unit 201 obtains data of the harvest achievement of grapes as harvest achievement data. This harvest achievement data is data of the harvest achievement of one grape harvesting work, and contains, for example, the harvest date/time, the yield, and the harvest range input by the user by using the input device 106. In this embodiment, the obtaining unit 201 accepts data input from the user by displaying a GUI 801 shown in FIG. 8 on the display device 105.

In the GUI 801, the user can select a section as a data input target, by operating a pulldown menu 802 by using the input device 106. The section c is selected in FIG. 8.

Figure 8:
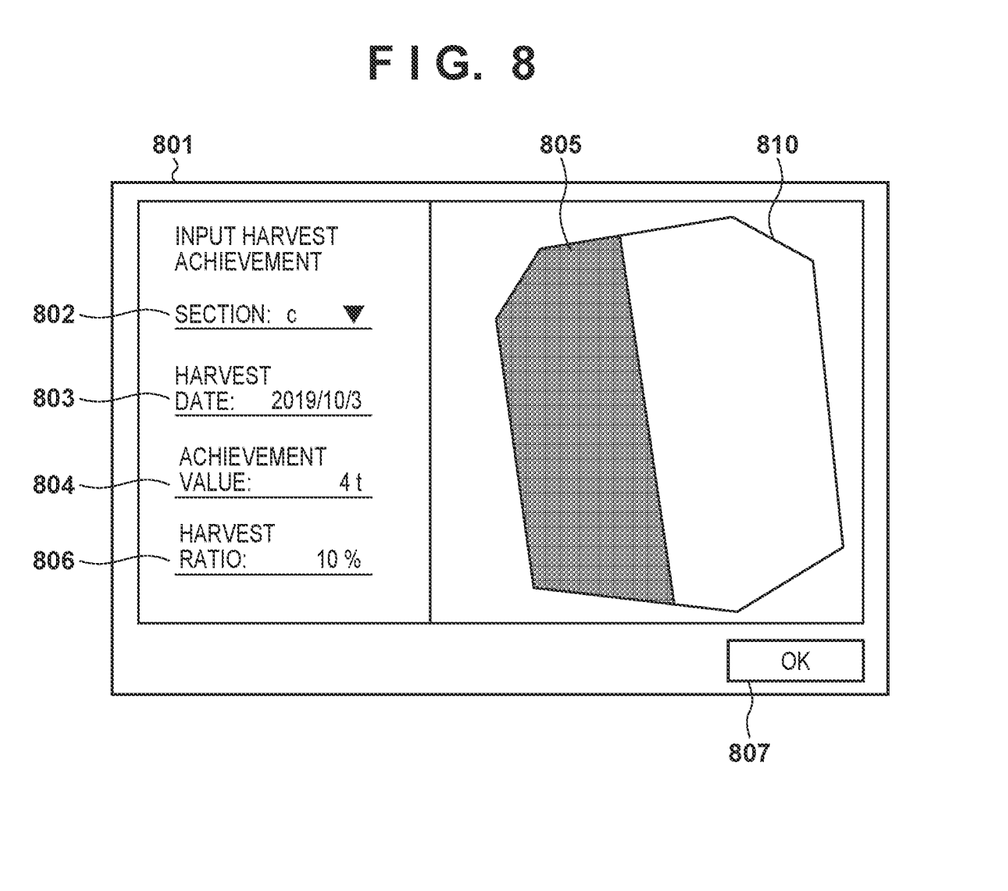
FIG. 8 is a view showing a display example of a GUI.

A polygon 810 is a polygonal image defined by "the positions of vertices corresponding to section ID=c of a section selected in the pulldown menu 802" registered in the section table 508.

The user can also input, to a region 803, the date/time (harvest date/time) at which one harvesting of grapes is performed once in the section (the section c in FIG. 8) selected in the pulldown menu 802, by using the input device 106.

Furthermore, the user can input, to a region 804, the amount of grapes (harvest achievement) harvested in the section (the section c in FIG. 8) selected in the pulldown menu 802, by using the input device 106.

In addition, the user can designate a corresponding range in the polygon 810 corresponding to the range (harvest range) in which grapes are harvested in the section c, by using the input device 106. In FIG. 8, a gray region 805 is designated as the corresponding range. Note that the user can input "the ratio of the harvest range in the section c" (10% in FIG. 8) to a region 806 by using the input device 106, without designating the region 805. In this case, data to be input to the region 806 is the areal ratio of the harvested range in the whole section. However, it is sometimes difficult to require the user to input an accurate numerical value, or contradiction sometimes occurs to some extent with respect to the size of the region designated in the polygon 810. In this embodiment, therefore, if the harvested range is designated on the map like the region 805, this designation is used preferentially to the input to the region 806.

Figure 9A:
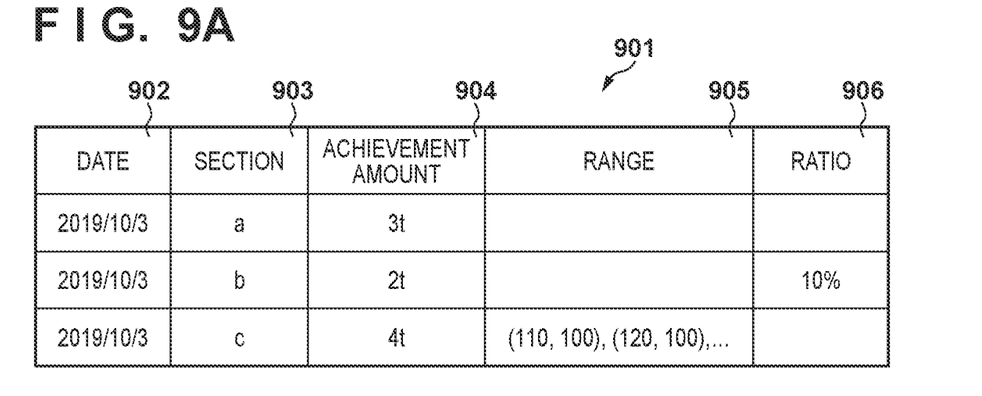
FIG. 9A is a view showing a configuration example of a table.

Then, when the user clicks an OK button 807 by using the input device 106, the obtaining unit 201 registers the harvest achievement data containing the group of data input by using the GUI 801 shown in FIG. 8, in a table 901 shown in FIG. 9A. The harvest achievement data is registered in each row of the table 901 shown in FIG. 9A.

In a column 902, the harvest date/time input in the region 803 is registered. In a column 903, the section ID of the section selected in the pulldown menu 802 is registered. In a column 904, the harvest achievement input in the region 804 is registered. In a column 905, the positions of vertices defining the corresponding range are registered. In a column 906, the ratio input in the region 806 is registered. Note that no numerical values need be registered in the columns 905 and 906.

Referring to FIG. 7 again, in step S702, an estimation unit 203 obtains the total amount (the total yield) of harvested grapes in the section selected in the pulldown menu 802, and the total amount (the total unharvested amount) of unharvested grapes in the section. Details of the processing in step S702 will be explained with reference to a flowchart shown in FIG. 10. A case in which the section selected in the pulldown menu 802 is the section c will be explained below, but the same processing is performed even when the section a (the section of section ID=a) or the section b (the section of section ID=b) is selected.

Figure 10:
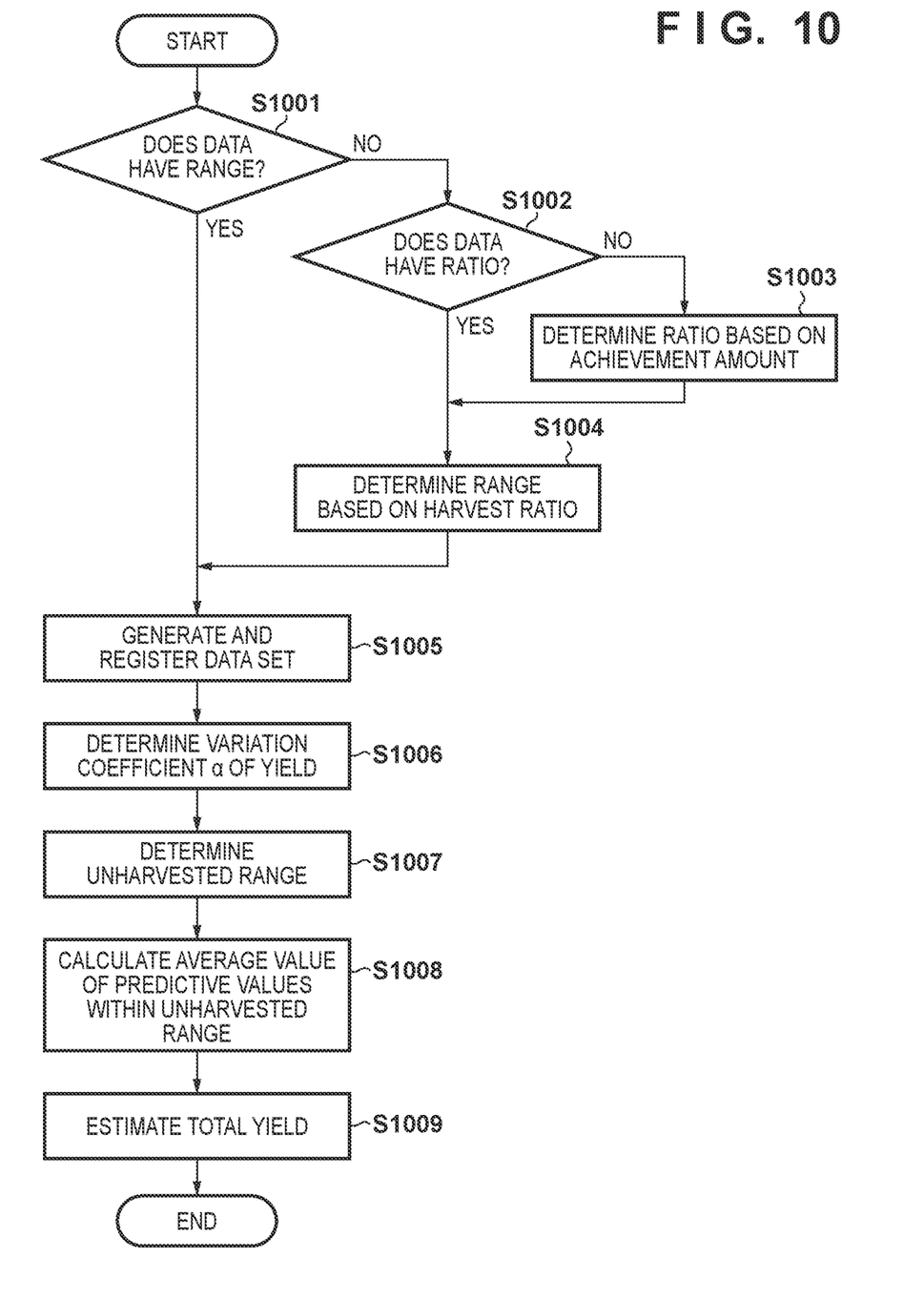
FIG. 10 is a flowchart showing details of processing in step S702.

In step S1001, the estimation unit 203 determines whether harvest achievement data corresponding to the section c contains "the positions of vertices defining the corresponding range" (range data). If the determination result is YES, the process advances to step S1005. If the determination result is NO, the process advances to step S1002.

In step S1002, the estimation unit 203 determines whether the harvest achievement data corresponding to the section c contains "the ratio". If the determination result is YES, the process advances to step S1004. If the determination result is NO, the process advances to step S1003.

In step S1003, the estimation unit 203 obtains the ratio of the harvest range in the section c by using the section table 508, the predictive yield table 513, and the table 901.

For example, the estimation unit 203 obtains the predictive yields corresponding to section ID=c from the predictive yield table 513, and calculates the average value of the obtained predictive yields. Then, the estimation unit 203 obtains an area corresponding to section ID=c from the section table 508, and calculates the product of the obtained area and the average value of the predictive yields corresponding to section ID=c, as "an expected yield X in the section c". Subsequently, the estimation unit 203 calculates ("harvest achievement" contained in the harvest achievement data of the section c)/(the expected yield X in the section c), as the ratio corresponding to the section c.

In step S1004, the estimation unit 203 obtains the positions of vertices in a corresponding range that corresponds to the harvest range, in the polygonal region of the section c. For example, the estimation unit 203 performs the following processing in order to obtain the positions of vertices of the corresponding range for section ID=c. First, the estimation unit 203 obtains an area corresponding to section ID=c from the section table 508, and calculates the product of the area and the ratio ("the ratio" contained in the harvest achievement data or the ratio calculated in step S1003) as an area S. Then, the estimation unit 203 obtains "the positions of vertices" corresponding to section ID=c from the section table 508, and specifies a range having the area S in the polygonal region defined by "the positions of vertices", as the corresponding range. After that, the estimation unit 203 specifies the positions of vertices of the corresponding range. Note that if there is no harvested range, a predetermined range may also be selected.

That is, the process advances to step S1005 via step S1001 for harvest achievement data containing "the positions of vertices defining the corresponding range" (range), among the harvest achievement data corresponding to the section c. Also, the process advances to step S1005 via steps S1001, S1002, and S1004 for harvest achievement data not containing the range but containing "the ratio", among the harvest achievement data corresponding to the section c. Furthermore, the process advances to step S1005 via steps S1001, S1002, S1003, and S1004 for harvest achievement data containing neither the range nor "the ratio", among the harvest achievement data corresponding to the section c.

Figure 9B:
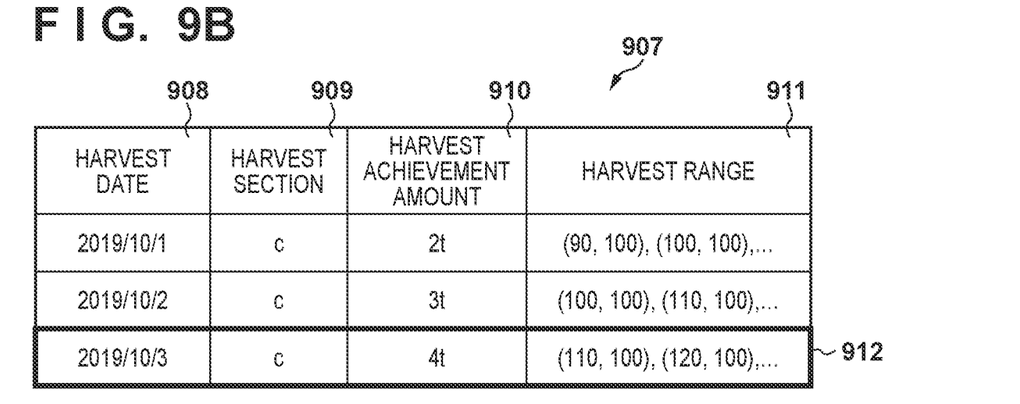
FIG. 9B is a view showing a configuration example of a harvest achievement data table 907.

In step S1005, the estimation unit 203 generates a data set containing the positions of vertices of the corresponding range in the polygonal region of the section c, and registers the data set in a harvest achievement data table. FIG. 9B shows a configuration example of a harvest achievement data table 907.

The harvest date/time corresponding to section ID=c in the table 901 is registered in a column 908, and section ID=c is registered in a column 909. The harvest achievement corresponding to section ID=c in the table 901 is registered in a column 910. "The positions of vertices" in the harvest achievement data of the section c or "the positions of vertices of the corresponding range" specified for the section c in step S1004 are registered in a column 911.

Then, in step S1006, the estimation unit 203 calculates a variation coefficient $\alpha$ of the yield of grapes in the section c. The variation coefficient $\alpha$ is a value to be used to reflect the property of a crop in a section to the progress of the yield. The property is, for example, a variation in growth state. For example, the estimation unit 203 performs the following processing in order to calculate the variation coefficient $\alpha$ of the yield of grapes in the section c. The estimation unit 203 obtains a data set containing an image capturing position included in a polygonal region R defined by "the positions of vertices" in a row 912 of recent harvest date/time in the harvest achievement data table 907, from the data sets in the rows registered in the predictive yield table 513. Note that if the number of obtained data sets is smaller than a threshold, the estimation unit 203 can further obtain all data sets containing section ID=c in the predictive yield table 513. Then, the estimation unit 203 obtains the predictive yields contained in the data sets obtained from the predictive yield table 513, and calculates an average value E of the obtained predictive yields. Subsequently, the estimation unit 203 calculates variation coefficient $\alpha=A/(E\times(\text{the area of the polygonal region R}))$ by using harvest achievement A in the abovementioned row 912 and the average value E, thereby obtaining the variable coefficient $\alpha$. The area of the polygonal region R is obtained by a function for calculating an area from information defining a region.

In step S1007, the estimation unit 203 specifies a remaining region obtained by omitting the polygonal region R from the polygonal region defined by "the positions of vertices corresponding to section ID=c" registered in the section table 508, as "an unharvested range", and calculates an area Su of this unharvested range. The area of the unharvested range is calculated by using a function for calculating an area from information defining a region.

Then, in step S1008, the estimation unit 203 calculates the average value of the predictive yields (predicted values) corresponding to the unharvested range. For example, the estimation unit 203 selects a row in which an image capturing position contained in the unharvested range is registered, from the rows of the predictive yield table 513. If the number of specified rows is smaller than a threshold, the estimation unit 203 further selects a row in which section ID=c is registered. Subsequently, the estimation unit 203 calculates an average value Eu of the predictive yields registered in the selected rows.

In step S1009, the estimation unit 203 calculates a total amount Yu of unharvested grapes in the section c. For example, the estimation unit 203 calculates $Yu=\alpha \times Eu \times Su$ by using the variation coefficient $\alpha$ calculated in step S1006, the area Su calculated in step S1007, and the average value Eu calculated in step S1008, thereby obtaining the total amount Yu of unharvested grapes in the section c. In addition, the estimation unit 203 calculates the sum of the harvest achievements registered in the column 910 of the harvest achievement data table 907, as a total amount Yh of harvested grapes in the section c.

Figure 11:
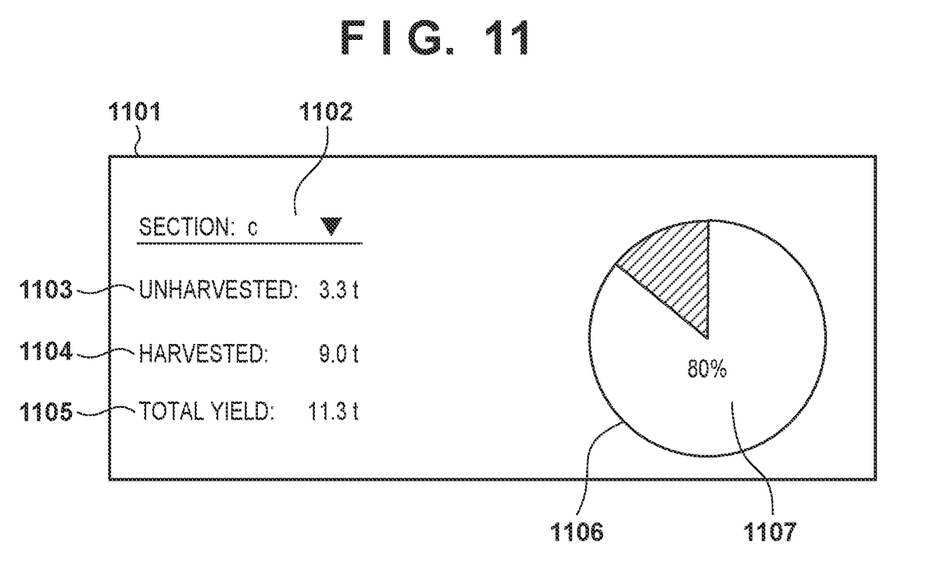
FIG. 11 is a view showing a display example of a screen showing the progress of harvesting of grapes in a section c.

Referring to FIG. 7 again, in step S703, the display unit 204 generates a screen representing the progress of harvesting of grapes in the section c, based on "the total amount Yu of unharvested grapes in the section c" and "the total amount Yh of harvested grapes in the section c" calculated in step S702. Then, the display unit 204 performs display control for displaying the generated screen on the display screen of the display device 105, thereby notifying the user of the progress. FIG. 11 shows a display example of the screen.

On the screen 1101 shown in FIG. 11, a region 1103 displays "the total amount Yu of unharvested grapes in the section c", and a region 1104 displays "the total amount Yh of harvested grapes in the section c". A region 1105 displays the sum of the total amount Yu displayed in the region 1103 and the total amount Yh displayed in the region 1104. The screen 1101 also displays a pie chart 1106 indicating the ratio of each of the total amounts Yu and Yh in the sum displayed in the region 1105, and a value "80%" indicates the ratio of the total amount Yh in the sum displayed in the region 1105. Thus, the screen 1101 displays information indicating the progress of harvesting of grapes in the section c.

The user can also select a section in which he or she wants to see the progress on the screen 1101, by operating a pulldown menu 1102 by using the input device 106. If the user selects another section (for example, the section b) by operating the pulldown menu 1102 by using the input device 106, the display unit 204 generates and displays a screen representing the progress of harvesting of grapes in the section based on the total amounts Yu and Yh calculated for the section in step S702.

Note that the configuration of the screen shown in FIG. 11 is merely an example, and does not intend to limit the present invention to the configuration like this. For example, it is unnecessary to display all the pieces of information shown in FIG. 11 as information to be displayed on the screen 1101. For example, the pie chart 1106 can be displayed when the user sets "display", and can also be displayed selectively in accordance with a user's operation. In addition, the information indicating the progress of harvesting of grapes is not limited to the ratio of the total amount Yh to the sum displayed in the region 1105 as described above, and may also be, for example, the ratio of the total amount Yu to the sum displayed in the region 1105. It is also possible to calculate the total amounts Yu and Yh for individual sections in step S702, and display pieces of information indicating the progresses in these sections in parallel on the screen 1101. It is further possible to collectively present the total yield and the progress of the same planted species.

According to this embodiment as described above, the total yield can be estimated by using the data of the predictive yield and the harvest achievement amount, and, when harvesting is partially performed in one section, the progress with respect to the total yield can be determined and presented. In addition, more accurate estimation can be performed by obtaining a variation in yield depending on a place in a section from the predictive yield based on data observed in each place. Especially in the cultivation of crops such as wine grapes to be processed after being harvested, planning of the processing step can be supported.

Second Embodiment

The difference from the first embodiment will be explained below, but the second embodiment is similar to the first embodiment unless otherwise specified. In the functional units shown in FIG. 2, the prediction unit 202 and the estimation unit 203 can execute the corresponding processes by using a learned model obtained by machine learning. In this case, a plurality of combinations of input data and output data for functional units such as the prediction unit 202 and the estimation unit 203 are prepared as learning data, knowledge is acquired from the learning data by machine learning, and a learned model that outputs data as results with respect to input data based on the acquired knowledge is generated. This learned model can be formed as a neural network model or the like. The learned model performs the processes of the prediction unit 202 and the estimation unit 203 by cooperating with a CPU or a GPU, as a computer program for executing processes equal to those of the prediction unit 202 and the estimation unit 203. Note that the abovementioned learned model can also be updated after predetermined processing as needed.

Also, the obtaining methods and the obtaining sources of various kinds of data explained in the first embodiment are examples, and are not limited to the obtaining methods and the obtaining sources explained above. In addition, the positions (the image capturing position and the positions of vertices) explained in the abovementioned processing can be positions on a real space and can also be positions so normalized as to fall within the range of the display screen of the display device 105. Furthermore, the configuration of the screen of the GUI used in the first embodiment is an example, and does not intend to limit the present invention to the configuration explained in the first embodiment. For example, information to be displayed and the display form are not limited to those explained above, and information displayed on one GUI/screen may also be displayed divisionally on two or more GUIs/screens. The two or more GUIs/screens can be displayed at the same time, and can also be displayed as they are switched by tabs or the like.

Information indicating the progress of harvesting of crops can be notified to the user by being displayed on the screen, and can also be notified to the user by another method. For example, the display unit 204 can notify a preset transmission destination of information indicating the progress of harvesting of crops by transmitting email describing the information to the transmission destination.

Note that the numerical values, the processing timings, the processing orders, and the like used in the abovementioned explanation are merely examples for making a practical explanation, and do not intend to limit the present invention to these numerical values, processing timings, and processing orders, and the like.

Note also that it is possible to appropriately use parts or the whole of the embodiments explained above by combining them, or selectively use the parts or the whole of the embodiments explained above.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-044387, filed Mar. 13, 2020, which is hereby incorporated by reference herein in its entirety.

What is claimed is:

1. An information processing apparatus comprising:
a processor; and
a memory, including instructions stored thereon, which when executed by the processor cause the apparatus to:
obtain a predicted value of a yield of crops in a section where the crops are cultivated;
obtain a yield of the crops harvested in the section; and
notify progress of harvesting of the crops in the section, which is determined based on the predicted value of the yield of the crops in the section and the yield of the crops harvested in the section;
wherein the second obtaining obtains a yield of the crops in a first region designated by a user operation as a region where partial harvesting is performed in the section,
wherein the progress of harvesting indicates, based on a property in the first region, a ratio of a yield of the crops harvested by the partial harvesting to a total amount of the yields of the crops, which is predicted in the section.

2. The apparatus according to claim 1, wherein the property in the first region is obtained based on data obtained by observing the crops in a position included in the first region.

3. The apparatus according to claim 2, wherein the instructions, when executed by the processor, further cause the apparatus to:
calculate a variation coefficient based on the yield obtained by the second obtaining, an average value of the predicted values obtained by the first obtaining for the first region, and an area of the first region; and calculate a total amount of unharvested crops based on an average value of the predicted values obtained by the first obtaining for a second region except the first region in the section, an area of the second region, and the variation coefficient, wherein the progress of harvesting is determined based on the yield obtained by the second obtaining and the total amount.

4. The apparatus according to claim 1, further comprising a display control unit for causing a display unit to display a screen for notifying the progress of harvesting of the crops in the section.

5. The apparatus according to claim 4, wherein the display control unit generates a screen containing a sum of the yields obtained by the second obtaining, a total amount of unharvested crops in the section, and a sum of the sum and the total amount.

6. The apparatus according to claim 4, wherein the display control unit generates a screen containing a ratio of a sum of the yields obtained by the second obtaining to a sum of the sum and a total amount of unharvested crops in the section.

7. The apparatus according to claim 1, wherein the first obtaining calculates a predicted value of a yield of the crops in the section, based on the number of crops per unit area of the section, and a preset weight of the crops in the section.

8. The apparatus according to claim 1, wherein the processing for the first obtaining, the second obtaining, and the notify progress of harvesting, are performed in each section of a crop cultivation region.

9. An information processing method to be performed by an information processing apparatus, comprising:

obtaining a predicted value of a yield of crops in a section where the crops are cultivated;

obtaining a yield of the crops harvested in the section; and notifying progress of harvesting of the crops in the section, which is determined based on the predicted value of the yield of the crops in the section, and the yield of the crops harvested in the section, wherein the second obtaining obtains a yield of the crops in a first region designated by a user operation as a region where partial harvesting is performed in the section, wherein the progress of harvesting indicates, based on a property in the first region, a ratio of a yield of the crops harvested by the partial harvesting to a total amount of the yields of the crops, which is predicted in the section.

10. A non-transitory computer-readable storage medium storing a computer program for an information processing method, the method comprising:

obtaining a predicted value of a yield of crops in a section where the crops are cultivated;

obtaining a yield of the crops harvested in the section; and notifying progress of harvesting of the crops in the section, which is determined based on the predicted value of the crops in the section and the yield of the crops harvested in the section, wherein the second obtaining obtains a yield of the crops in a first region designated by a user operation as a region where partial harvesting is performed in the section, wherein the progress of harvesting indicates, based on a property in the first region, a ratio of a yield of the crops harvested by the partial harvesting to a total amount of the yields of the crops, which is predicted in the section.

\* \* \* \* \*